United States Patent [19]
Dinsmore et al.

[11] Patent Number: 6,063,930
[45] Date of Patent: May 16, 2000

[54] SUBSTITUTED IMIDAZOLE COMPOUNDS USEFUL AS FARNESYL-PROTEIN TRANSFERASE INHIBITORS

[75] Inventors: Christopher J Dinsmore, Schwenksville; Neville J. Anthony, Hatfield; Gerald E. Stokker, Gwynedd Valley; Robert P. Gomez, Perkasie, all of Pa.

[73] Assignee: Merck & Co., Inc., Rahway, N.J.

[21] Appl. No.: 09/155,681

[22] PCT Filed: Apr. 1, 1997

[86] PCT No.: PCT/US97/06257

§ 371 Date: Oct. 2, 1998

§ 102(e) Date: Oct. 2, 1998

[87] PCT Pub. No.: WO97/36876

PCT Pub. Date: Oct. 9, 1997

Related U.S. Application Data

[60] Provisional application No. 60/014,592, Apr. 3, 1996.

[51] Int. Cl.$^7$ .................. C07D 213/24; C07D 213/30; C07D 233/58; C07D 233/64; A61K 31/44; A61K 31/4164

[52] U.S. Cl. .................. 546/337; 514/357; 514/399; 514/400; 546/345; 548/343.1; 548/346.1; 548/314.4

[58] Field of Search .............. 548/343.1, 346.1, 548/314.4; 546/337, 345; 514/357, 399, 400

[56] References Cited

U.S. PATENT DOCUMENTS

| | | | |
|---|---|---|---|
| 4,207,324 | 6/1980 | Matsumura et al. | 424/273 R |
| 4,749,713 | 6/1988 | Bowman et al. | 548/341 |
| 4,837,333 | 6/1989 | Manley et al. | 514/326 |
| 4,916,144 | 4/1990 | Strehlke et al. | 514/326 |
| 5,126,342 | 6/1992 | Chakravarty et al. | 514/235.8 |
| 5,219,856 | 6/1993 | Olson | 514/252 |
| 5,296,609 | 3/1994 | McCort et al. | 548/325.1 |
| 5,326,776 | 7/1994 | Winn et al. | 514/382 |
| 5,538,987 | 7/1996 | Salimbeni et al. | 514/341 |
| 5,559,141 | 9/1996 | Karjalainen et al. | 514/400 |
| 5,576,313 | 11/1996 | Fisher et al. | 514/211 |

FOREIGN PATENT DOCUMENTS

| | | |
|---|---|---|
| 0 648 763 A1 | 4/1995 | European Pat. Off. |
| 31 45 928 | 6/1983 | Germany . |
| 2273704 | 6/1994 | United Kingdom . |
| WO 93/13075 | 7/1993 | WIPO . |
| WO 94/08973 | 4/1994 | WIPO . |
| WO 95/00493 | 1/1995 | WIPO . |
| WO 96/30343 | 10/1996 | WIPO . |
| WO 96/34851 | 11/1996 | WIPO . |
| WO 96/37204 | 11/1996 | WIPO . |

OTHER PUBLICATIONS

Exp. Opin. Ther. Patents, vol. 5(12), pp. 1269–1285 (1995), by S. L. Graham.
Exp. Opin. Ther. Patents, vol. 6(12) (1996), pp. 1295–1304, by S. L. Graham, et al.
J. of Biol. Chem., vol. 268, No. 11, pp. 7617–7620 (1993), by J. B. Gibbs, et al.
J. of Biol. Chem., vol. 269, No. 44, pp. 27706–27714 (1994), by G. L. James, et al.
J. of Biol. Chem., vol. 270, No. 11, pp. 6221–6226 (1995), by G. L. James, et al.
Science, vol. 260, pp. 1934–1937 (1993), by N. E. Kohl, et al.
Proc. Natl. Acad. Sci. USA, vol. 91, pp. 9141–9145 (1994), by N. E. Kohl, et al.
Nature Medicine, vol. 1, No. 8, pp. 792–797 (1995), by N. E. Kohl, et al.
Cancer Research, vol. 55, pp. 5302–5309 (1995), by L. Sepp–Lorenzino, et al.

*Primary Examiner*—Floyd D. Higel
*Attorney, Agent, or Firm*—J. Antonio Garcia-Rivas; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

37 Claims, No Drawings

SUBSTITUTED IMIDAZOLE COMPOUNDS USEFUL AS FARNESYL-PROTEIN TRANSFERASE INHIBITORS

RELATED APPLICATIONS

This application is a § 371 of PCT/US97/06257 filed Apr. 1, 1997. This application claims the benefit of U.S. Provisional Application Ser. No. 60/014,592, filed Apr. 3, 1996.

BACKGROUND OF THE INVENTION

The present invention relates to compounds which inhibit farnesyl protein transferase, a protein which is implicated in the oncogenic pathway mediated by Ras. The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). Ras proteins are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific, and thus preferable.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)).

It has recently been reported that FPT-ase inhibitors also inhibit the proliferation of vascular smooth muscle cells and are therefore useful in the prevention and treatment of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

SUMMARY OF THE INVENTION

The present invention addresses a compound of formula I:

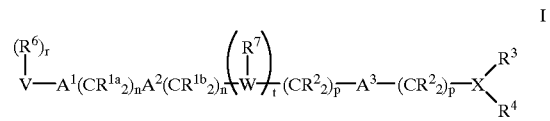

or a pharmaceutically acceptable salt thereof, wherein:
$R^{1a}$, $R^{1b}$ and $R^2$ are independently selected from the group consisting of: hydrogen, aryl, substituted aryl, heterocyclyl, $C_3$–$C_{10}$ cycloalkyl, $C_2$–$C_6$ alkenyl, $C_2$–$C_6$ alkynyl, $R^8O$—, $R^9S(O)_m$— wherein m is 0, 1 or 2, $R^8C(O)NR^8$—, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl, unsubstituted or substituted by 1–3 groups selected from the group consisting of: halo, aryl, heterocyclyl, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

$R^3$ and $R^4$ are independently selected from the group consisting of: H, F, Cl, Br, —$NR^8_2$, $CF_3$, $NO_2$, $R^8O$—, $R^9S(O)_m$—, $CF_3(CH_2)_g$—O—, $R^8C(O)NH$—, $H_2NC(NH)$—, $R^8C(O)$—, $R^8OC(O)$—, $N_3$, CN, $R^9OC(O)NR^8$—, $C_1$–$C_{20}$ alkyl, substituted or unsubstituted aryl and substituted or unsubstituted heterocyclyl;

$A^3$ is selected from: —C≡C—, —$R^8C=CR^8$—, —C(O)—, aryl, heteroaryl or a bond; provided that when $A^3$ is heteroaryl, attachment of $A^3$ the remainder of the molecule is through substitutable heteroaryl ring carbons;

X represents aryl or heteroaryl; provided that when X is heteroaryl, attachment of X the remainder of the molecule is through substitutable heteroaryl ring carbons;

$R^6$ is independently selected from the group consisting of: hydrogen, aryl, heterocyclyl, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^8O$—, $R^9S(O)_m$—, $R^8C(O)NR^8$—, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl unsubstituted or substituted by 1–3 groups selected from: aryl, heterocyclyl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

$R^7$ is independently selected from the group consisting of: hydrogen, aryl, heterocyclyl, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^9O$—, $R^9S(O)_m$—, $R^8C(O)NR^8$, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl unsubstituted or substituted by 1–3 groups selected from: aryl, heterocyclyl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

each $R^8$ is independently selected from hydrogen, $C_1$–$C_6$ alkyl, aryl and aralkyl;

each $R^9$ is independently selected from $C_1$–$C_6$ alkyl and aryl;

$A^1$ and $A^2$ are independently selected from the group consisting of: a bond, —CH=CH—, —C≡C—, —C(O)—, —C(O)$NR^8$—, —$NR^8C(O)$—, —O—, —$N(R^8)$—, —$S(O)_2N(R^8)$—, —$N(R^8)S(O)_2$—, and $S(O)_m$;

V is selected from the group consisting of: hydrogen, heterocyclyl, aryl, $C_1$–$C_{20}$ alkyl wherein from 0 to 4 carbon atoms are replaced with a heteroatom selected from O, S, and N, and $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

provided that when V is heterocyclyl, attachment of V to $R^6$ and to $A^1$ is through a substitutable ring carbon;

W represents heterocyclyl;

each n and p independently represents 0, 1, 2, 3 or 4;

r is 0 to 5, provided that r is 0 when V is hydrogen, and t is 1.

DETAILED DESCRIPTION OF THE INVENTION

The compounds of this invention are useful in the inhibition of farnesyl-protein transferase and the farnesylation of the oncogene protein Ras, and thus are useful for the treatment of cancer.

The compounds of the present invention may have asymmetric centers and occur as racemates, racemic mixtures and as individual diastereomers, with all possible isomers, including optical isomers, being included in the present invention.

When any variable (e.g. aryl, heterocycle, $R^1$, $R^2$ etc.) occurs more than one time in any constituent, each definition is independent.

The term "alkyl" and the alkyl portion of alkoxy, aralkyl and similar terms, is intended to include branched and straight-chain saturated aliphatic hydrocarbon groups having the specified number of carbon atoms, or 1–6 carbon atoms if unspecified. Cycloalkyl means 1–2 carbocyclic rings which are saturated and contain from 3–10 atoms.

"Halogen" or "halo" as used herein means fluoro, chloro, bromo and iodo.

As used herein, "aryl" and the aryl portion of aralkyl, are intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl. A preferred aralkyl group is benzyl.

The terms heterocyclyl, heterocycle and heterocyclic, as used herein, mean a 5- to 7-membered monocyclic or 9- to 11-membered bicyclic heterocyclic rings, either saturated or unsaturated, aromatic, partially aromatic or non-aromatic, and which consist of carbon atoms and from one to four heteroatoms selected from the group consisting of N, O, and S. Thus, it includes any bicyclic group in which any of the above-defined heterocyclic rings is fused to a benzene ring. The ring or ring system may be attached at any heteroatom or carbon atom which results in a stable structure. It optionally contains 1–3 carbonyl groups. Examples of such heterocycles include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopyrrolidinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl and thienyl.

"Heteroaryl" is a subset of heterocyclic as defined above, and means a monocyclic or bicyclic ring system, with up to 7 members in each ring, wherein at least one ring is aromatic and wherein from one to four carbon atoms are replaced by heteroatoms selected from the group consisting of N, O and S. Examples include benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl and thienyl.

Lines drawn into ring systems from substituents indicate that the bond may be attached to any of the substitutable ring carbon atoms.

Substituted alkyl, substituted aryl, substituted heterocyclyl and substituted cycloalkyl mean alkyl, aryl, heterocyclyl and cycloalkyl groups, respectively, having from 1–3 substituents which are selected from: halo, aryl, heterocyclyl, $C_{3-10}$ cycloalkyl, $C_{2-6}$ alkenyl, $C_{2-6}$ alkynyl, $R^8O-$, $R^9S(O)_m-$, $R^8C(O)NR^8-$, CN, $(R^8)_2NC(NR^8)-$, $R^8C(O)-$, $R^8OC(O)-$, $N_3$, $-N(R^8)_2$ and $R^9OC(O)NR^8-$. When for example, a substituted alkyl group is substituted with a "substituted aryl group", the aryl portion is substituted with 1–3 groups as defined above.

Preferably 1–2 groups are present on substituted alkyl, substituted aryl, substituted heterocyclyl and substituted cycloalkyl, which are selected from: halo, aryl, $R^8O-$, CN, $R^8C(O)-$ and $-N(R^8)_2$.

Preferably, $R^{1a}$, $R^{1b}$ and $R^2$ are independently selected from: hydrogen, $-N(R^8)_2$, $R^8C(O)NR^8-$ or unsubstituted or substituted $C_1-C_6$ alkyl wherein the substituent on the substituted $C_1-C_6$ alkyl is selected from unsubstituted or substituted aryl, $-N(R^8)_2$, $R^8O-$ and $R^8C(O)NR^8-$.

Preferably, $R^3$ and $R^4$ are selected from: hydrogen, $C_1-C_6$ alkyl, Br, Cl, F, $R^8O-$, and $CF_3$.

In a preferred group of compounds, $A^3$ represents $-C\equiv C-$, $-CR8=CR8-$, $-C(O)-$ or a bond. A particularly preferred group of compounds within this subset includes compounds of formula I wherein $A^3$ represents $-C\equiv C-$ or a bond.

Another preferred group of compounds includes the compounds of formula I wherein $A^3$ represents aryl or heteroaryl.

Preferably $R^6$ represents CN.

Preferably, $R^7$ represents hydrogen, unsubstituted or substituted $C_1-C_6$ alkyl.

Preferably, $R^8$ represents H or $C_{1-6}$ alkyl, and $R^9$ is $C_{1-6}$ alkyl.

Preferably, $A^1$ and $A^2$ are independently selected from: a bond, $-C(O)NR^8-$, $-NR^8C(O)-$, $-O-$, $-N(R^8)-$, $-S(O)_2N(R^8)-$ and $-N(R^8)S(O)_2-$.

Preferably, V is selected from hydrogen, heterocyclyl and aryl. More preferably V is phenyl.

Preferably, W is heterocyclyl selected from imidazolinyl, imidazolyl, oxazolyl, pyrazolyl, pyyrolidinyl, thiazolyl and pyridyl. More preferably, W is selected from imidazolyl and pyridyl.

Preferably X represents aryl. In particular, X can represent phenyl.

Preferably, m is 0 or 2.

Preferably n and p are 0, 1, 2 or 3.

A subset of compounds of the invention is represented by formula Ia:

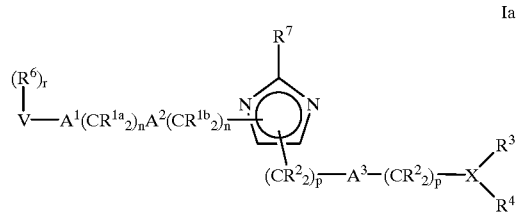

wherein:
$R^3$, $R^4$, $A^3$, $R^8$, $R^9$, X, m, n, p and r are as originally defined;
each $R^{1a}$ and $R^2$ is independently selected from hydrogen and $C_1-C_6$ alkyl;
each $R^{1b}$ is independently selected from: hydrogen, aryl, heterocyclyl, $C_{3-10}$ cycloalkyl, $C_{2-6}$ alkenyl, $R^8O-$, $-N(R^8)_2$ and $C_1-C_6$ alkyl unsubstituted or substituted by aryl, heterocyclyl, cycloalkyl, alkenyl, $R^8O-$ and $-N(R^8)_2$;
$R^6$ is independently selected from: hydrogen, $C_1-C_6$ alkyl, $C_2-C_6$ alkenyl, $C_2-C_6$ alkynyl, $C_1-C_6$ perfluoroalkyl, F, Cl, $R^8O-$, $R^8C(O)NR^8-$, CN, $NO_2$, $(R^8)_2N-C(NR^8)-$, $R^8C(O)-$, $R^8OC(O)-$, $-N(R^8)_2$, or $R^9OC(O)NR^8-$, and $C_1-C_6$ alkyl substituted by $C_1-C_6$ perfluoroalkyl, $R^8O-$, $R^8C(O)NR^8-$, $(R^8)_2N-C(NR^8)-$, $R^8C(O)-$, $R^8OC(O)-$, $-N(R^8)_2$ and $R^9OC(O)NR^8-$;
$R^7$ represents H or $C_{1-6}$ alkyl;
$A^1$ and $A^2$ are independently selected from: a bond, $-CH=CH-$, $-C\equiv C-$, $-C(O)-$, $-C(O)NR^8-$, O, $-N(R^8)-$ and $S(O)_m$;
and V is selected from: hydrogen; aryl; heterocyclyl selected from pyrrolidinyl, imidazolyl, pyridinyl, thiazolyl, indolyl, quinolinyl, isoquinolinyl and thienyl; $C_1-C_{20}$ alkyl wherein from 0 to 4 carbon atoms are replaced with a a heteroatom selected from O, S, and N, and $C_2-C_{20}$ alkenyl, provided that V is not hydrogen if $A^1$ is $S(O)_m$ and V is not hydrogen if $A^1$ is a bond and $A^2$ is $S(O)_m$; provided that when V is heterocycle, attachment of V to $R^6$ and to $A^1$ is through a substitutable ring carbon.

A second subset of compounds of the present invention is represented by formula Ib:

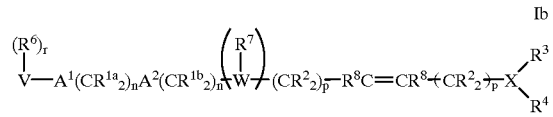

wherein:
$R^{1a}$, $R^{1b}$, $R^2$, $A^1$, $A^2$, $R^3$, $R^4$, $R^6$, $R^8$, $R^9$, X, m, n, p and r are as originally defined;
$R^7$ is selected from: hydrogen and $C_1-C_6$ alkyl;
V is selected from: hydrogen, heterocyclyl selected from pyrrolidinyl, imidazolyl, pyridinyl, thiazolyl, indolyl, quinolinyl, isoquinolinyl and thienyl; aryl; $C_1-C_{20}$ alkyl wherein from 0 to 4 carbon atoms are replaced with a heteroatom selected from O, S, and N, and $C_2-C_{20}$ alkenyl,
provided that V is not hydrogen if $A^1$ is $S(O)_m$ and V is not hydrogen if $A^1$ is a bond, n is 0 and $A^2$ is $S(O)_m$; provided that when V is heterocycle, attachment of V to $R^8$ and to $A^1$ is through a substitutable ring carbon; and W represents heterocyclyl selected from pyrrolidinyl, imidazolyl, pyridinyl, thiazolyl, indolyl, quinolinyl and isoquinolinyl.

A third subset of compounds of the present invention is represented by formula Ic:

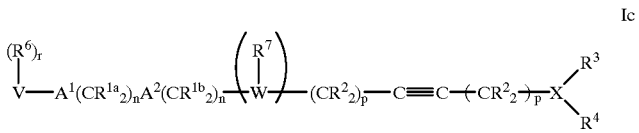

Ic wherein:

$R^{1a}$, $R^{1b}$, $R^2$, $A^1$, $A^2$, $R^3$, $R^4$, $R^6$, $R^8$, $R^9$, X, m, n, p and r are as originally defined;

$R^7$ is selected from: hydrogen and $C_1$–$C_6$ alkyl;

V is selected from: hydrogen, heterocyclyl selected from pyrrolidinyl, imidazolyl, pyridinyl, thiazolyl, indolyl, quinolinyl, isoquinolinyl, and thienyl, aryl, $C_1$–$C_{20}$ alkyl wherein from 0 to 4 carbon atoms are replaced with a heteroatom selected from O, S, and N, and $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$; provided that when V is heterocycle, attachment of V to $R^8$ and to $A^1$ is through a substitutable ring carbon; and W represents heterocyclyl selected from pyrrolidinyl, imidazolyl, pyridinyl, thiazolyl, indolyl, quinolinyl and isoquinolinyl.

A fourth embodiment of the invention is described in accordance with formula Id:

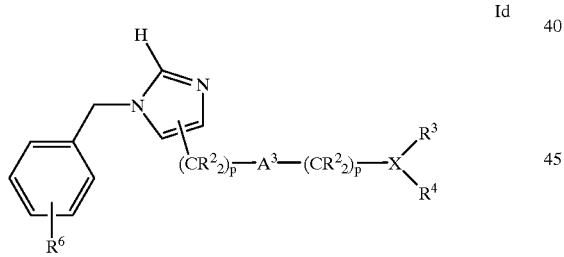

Id wherein:

each $R^2$ is independently selected from hydrogen and $C_1$–$C_6$ alkyl;

$R^3$, $R^4$, $A^3$, $R^8$, $R^9$, X, m and p are as originally defined;

and $R^6$ is selected from the group consisting of: hydrogen, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—C(NR^8)—, $R^8C(O)$—, $R^8OC(O)$—, —$N(R^8)_2$, or $R^9OC(O)NR^8$— and $C_1$–$C_6$ alkyl substituted by $C_1$–$C_6$ perfluoroalkyl, $R^8O$—, $R^8C(O)NR^8$—, $(R^8)_2N$—C(NR^8)—, $R^8C(O)$, $R^8OC(O)$—, —$N(R^8)_2$ or $R^9OC(O)NR^8$—.

A fifth subset of compounds of the invention is represented by formula Ie:

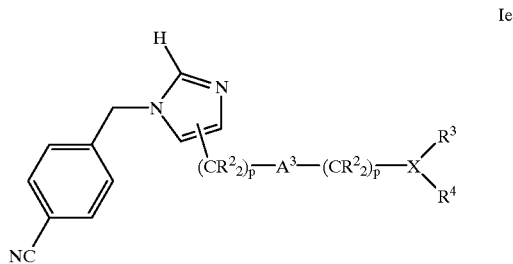

Ie wherein:

X and $A^3$ are as originally defined;

each $R^2$ is independently selected from: hydrogen and $C_1$–$C_6$ alkyl;

$R^3$ and $R^4$ are independently selected from H, F, Cl, Br, $N(R^8)_2$, $CF_3$, $NO_2$, $(R^8)O$—, $(R^9)S(O)_m$—, $(R^8)C(O)NH$—, $H_2N$—C(NH)—, $(R^8)C(O)$—, $(R^8)OC(O)$—, $N_3$, CN, $(R^9)OC(O)NR^8$—, $C_1$–$C_{20}$ alkyl, substituted or unsubstituted aryl, and substituted or unsubstituted heterocyclyl;

and $R^8$, $R^9$, m and p are as originally defined.

Specific examples of compounds of the invention are:

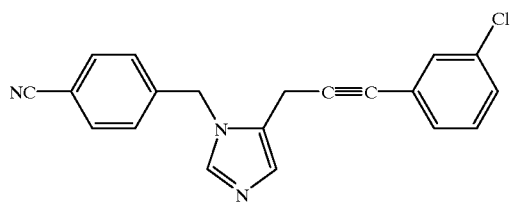

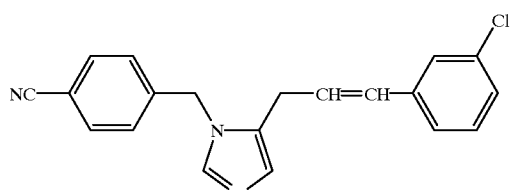

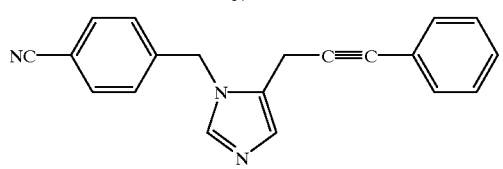

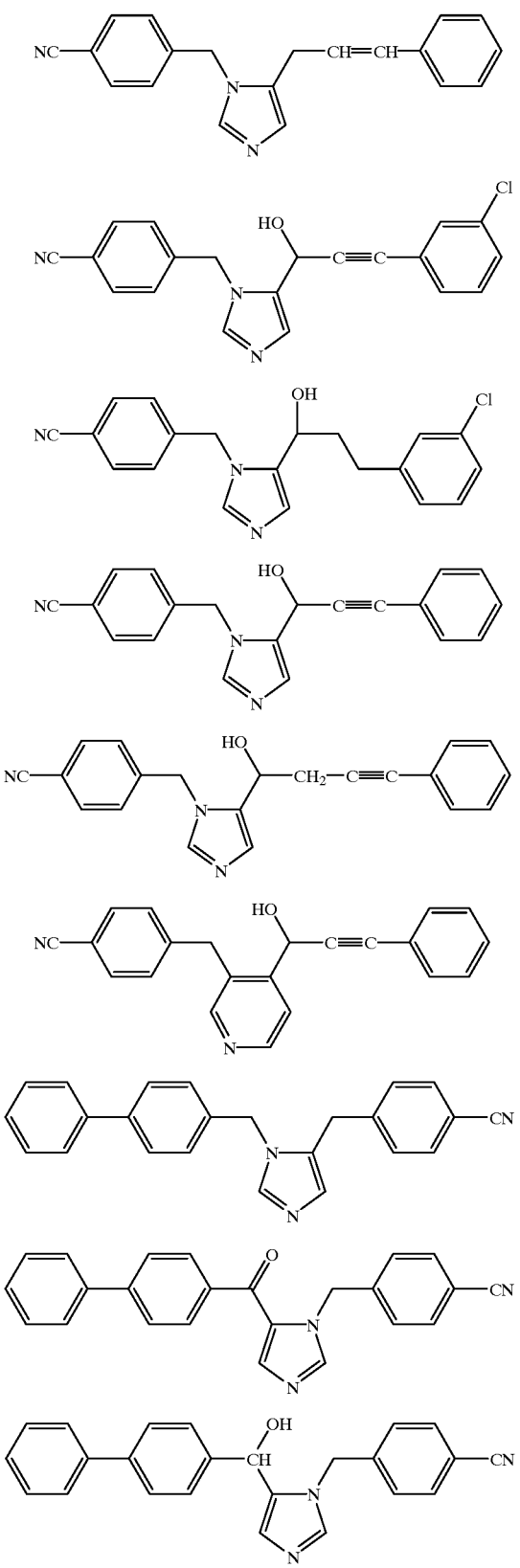

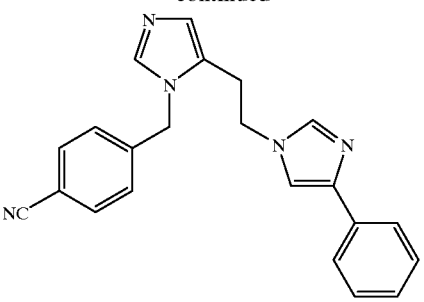

and the pharmaceutically acceptable salts and isomers thereof.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes, in addition to other standard manipulations such as ester hydrolysis, cleavage of protecting groups, etc., as may be known in the literature or exemplified in the experimental procedures. Substituents R' and R'CH$_2$—, as shown in the Schemes, represent the substituents R$^8$, R$^9$ and others, depending on the compound of the instant invention that is being synthesized. The variable p' represents p-1.

These reactions may be employed in a linear sequence to provide the compounds of the invention or they may be used to synthesize fragments which are subsequently joined by the alkylation reactions described in the Schemes.

Synopsis of Schemes

The requisite intermediates are in some cases commercially available, or can be prepared according to literature procedures. Schemes 1–2 illustrate the synthesis of one of the preferred embodiments of the instant invention, wherein the variable W is present as an imidazolyl moiety that is substituted with a suitably substituted benzyl group. Substituted protected imidazoles can be prepared by methods such as those described by F. Schneider, *Z. Physiol. Chem.*, 3:206–210 (1961) and C. P. Stewart, *Biochem. Journal*, 17:130–133(1923). Benzylation and deprotection of the imidazole alkanol provides intermediate III which can be oxidized to the corresponding aldehyde IV. Also, while X is shown as a phenyl ring, other aryl and heteroaryl groups can be substituted therein without departing from the invention.

The aldehyde whose synthesis is illustrated in Scheme 1 may be reacted with a suitably substituted aralkyne, to provide the intermediate compound V. Compound V can be selectively hydrogenated across the unsaturated bond under standard conditions, such as those illustrated, to provide Compound VI.

Schemes 3–10 illustrate syntheses of suitably substituted aldehydes useful in the syntheses of the instant compounds wherein the variable W is a pyridyl moiety. Similar synthetic strategies for preparing alkanols that incorporate other heterocyclic moieties for variable W can be discerned from the teachings herein.

Generally the aldehyde is reacted with an appropriately substituted aralkyne using n-BuLi, after which the triple bond can be reduced. As shown in Schemes 2, 4, 6 and 8 reduction of the alkyne triple bond using Pd/BaSO4 lproduces the Z-olefin isomer almost exclusively. By substituting sodium bis(2-methoxyethoxy)aluminum hydride (RED-AL) in toluene, one can readily obtain the E-allylic alcohol from propargylic alkynes used in the present invention.

In the preparation methods described herein, reactive groups may remain blocked until the final product is prepared, essentially in protected form, after which a final deprotection step is conducted. These blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile and catalytic hydrogenation.

Examples of suitable hydroxyl protecting groups are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Preferred hydroxyl protecting groups are trimethylsilyl and triethylsilyl.

Examples of suitable carboxyl protecting groups are: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. A preferred carboxyl protecting group is p-nitrobenzyl.

Many other suitable hydroxyl and carboxyl protecting groups are known in the art. See, e.g., T. W. Greene, *Protective Groups in Organic Synthesis*, John Wiley & Sons, Inc., 1981 (Chapters 2 and 5).

SCHEME 1

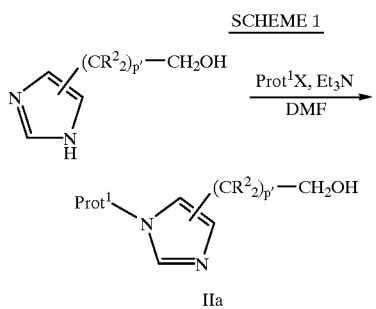

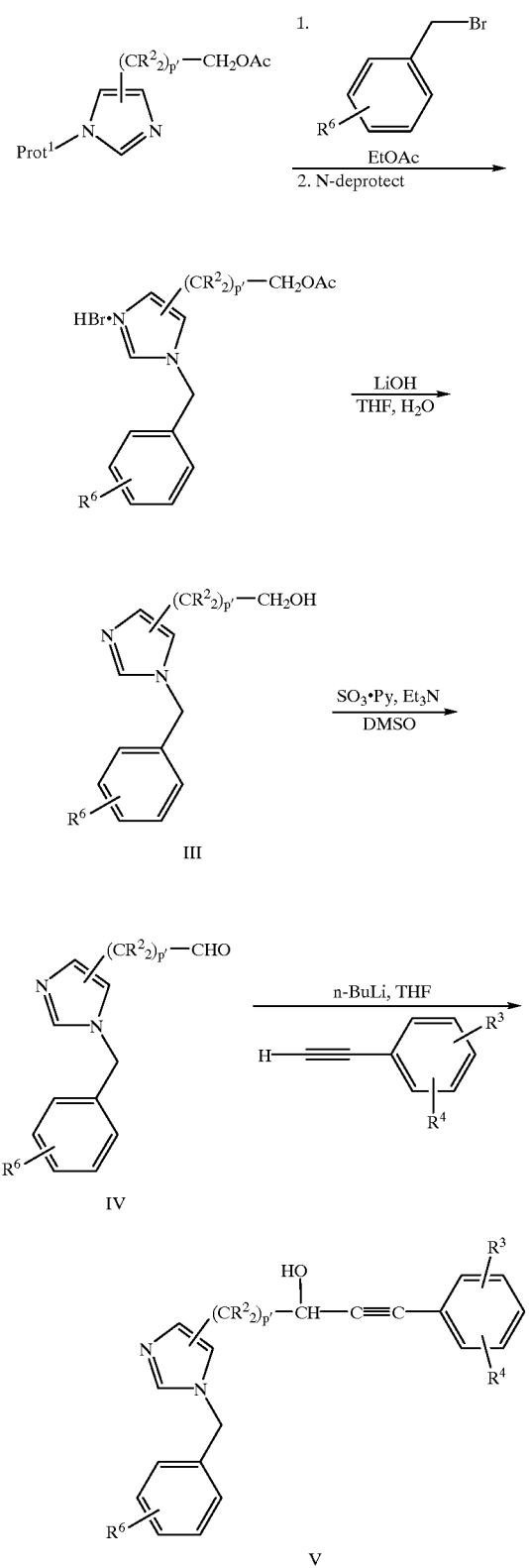

SCHEME 2
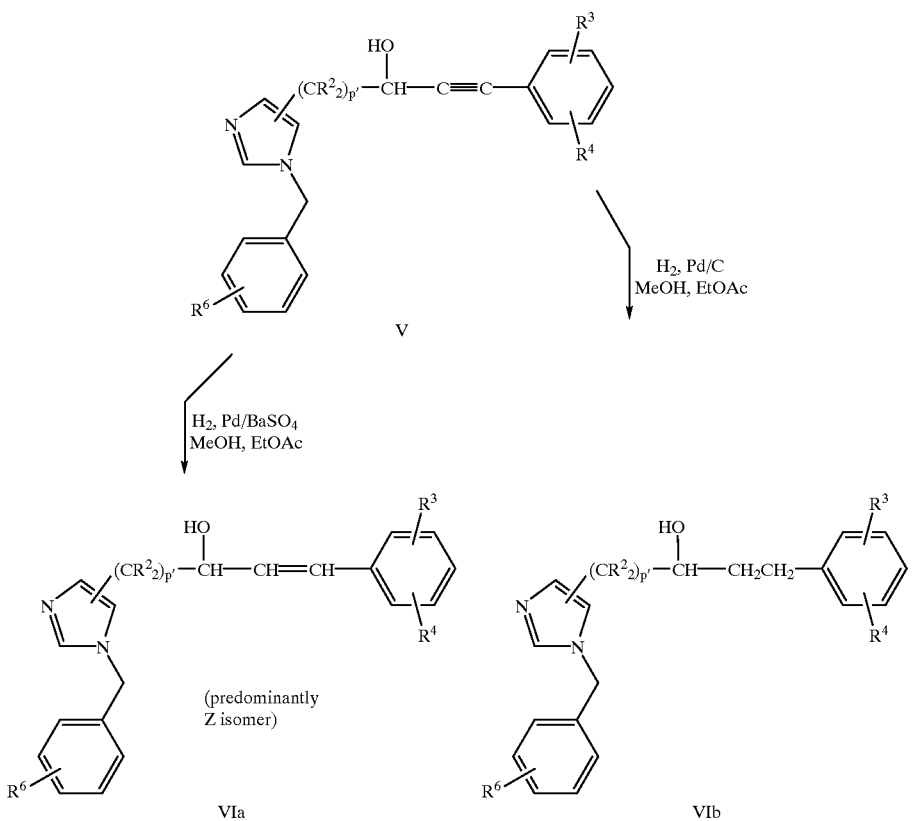
SCHEME 3
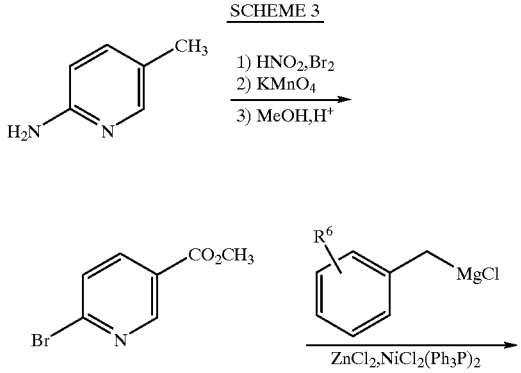
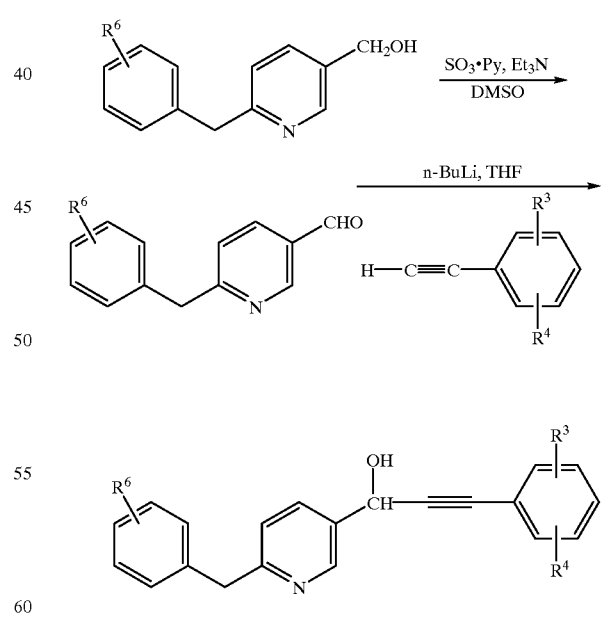

SCHEME 4
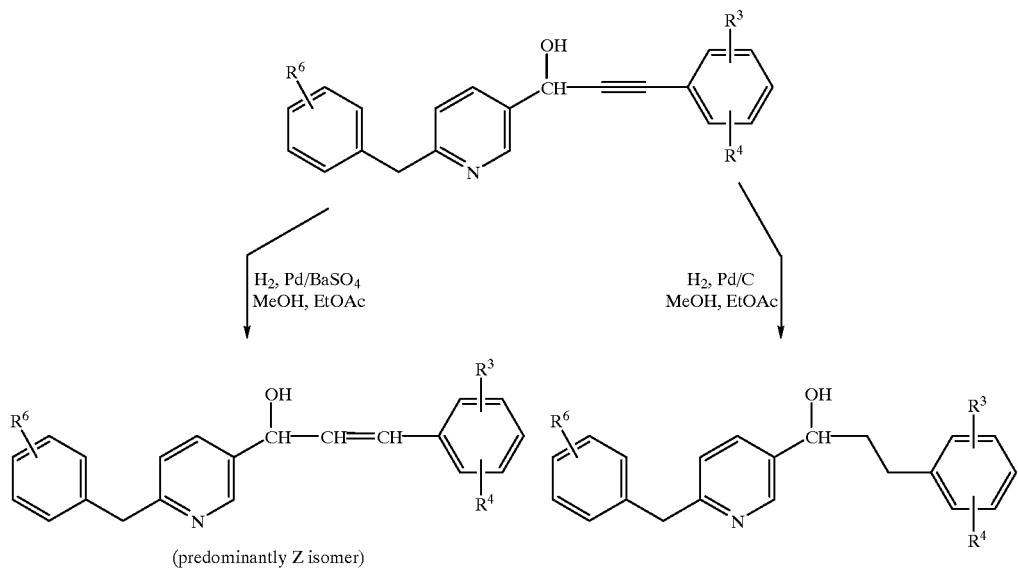
(predominantly Z isomer)
SCHEME 5
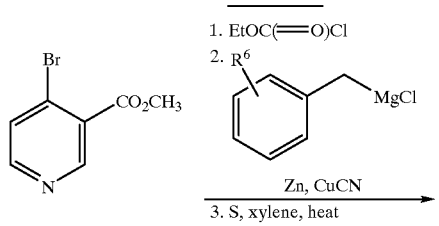
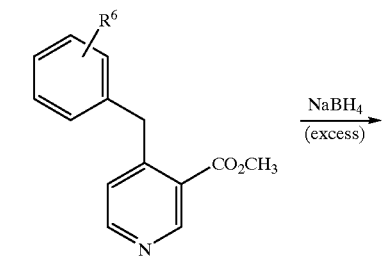
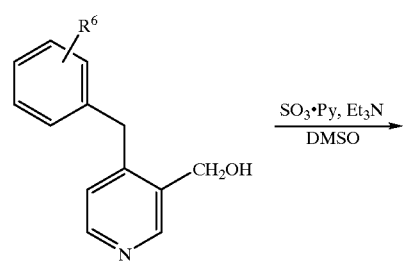
-continued
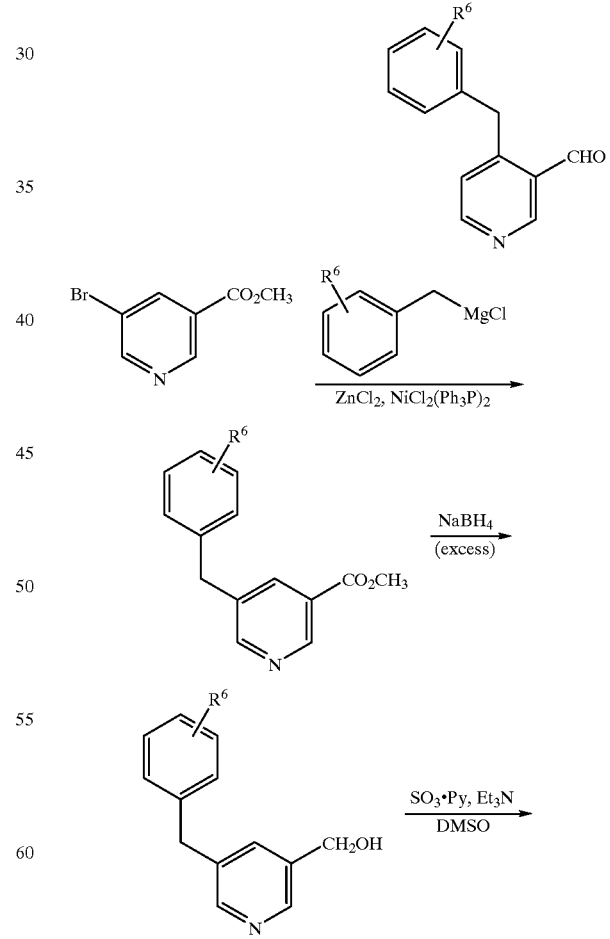

17
-continued
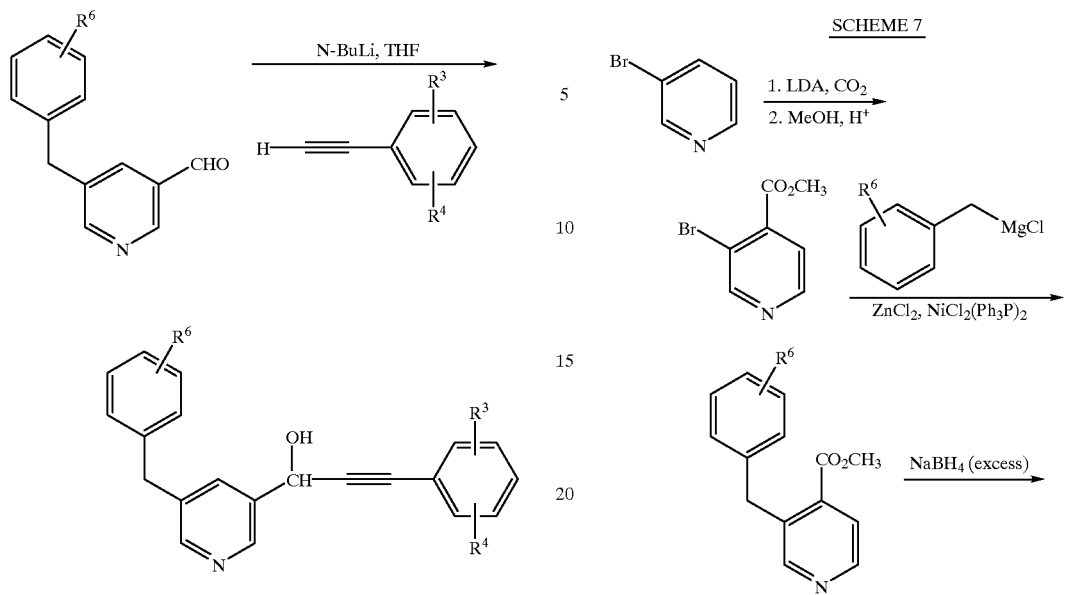
SCHEME 7
SCHEME 6
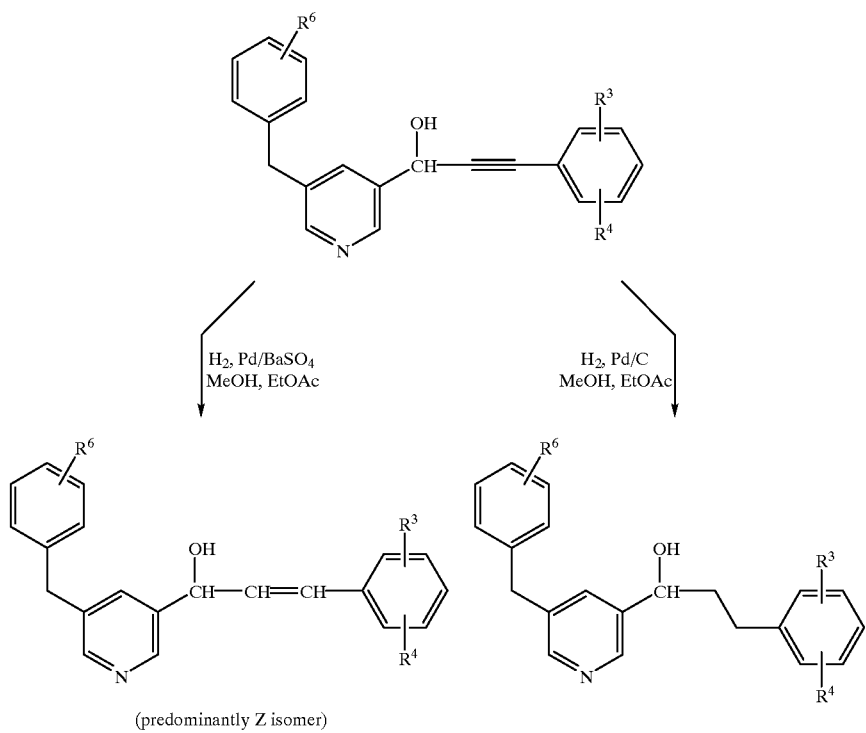

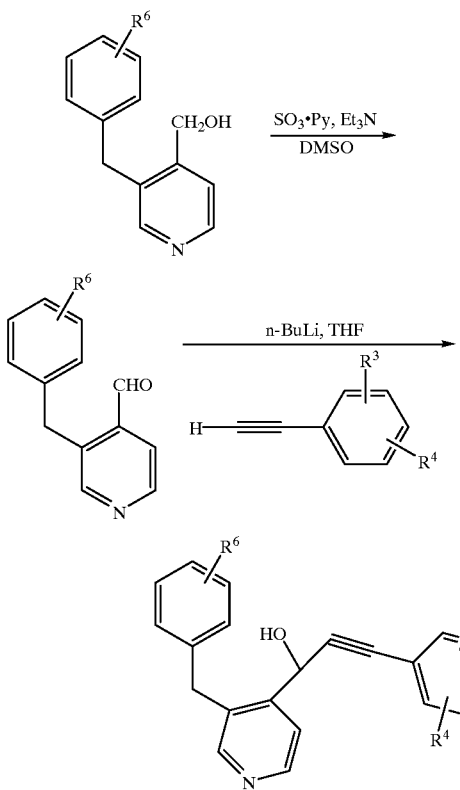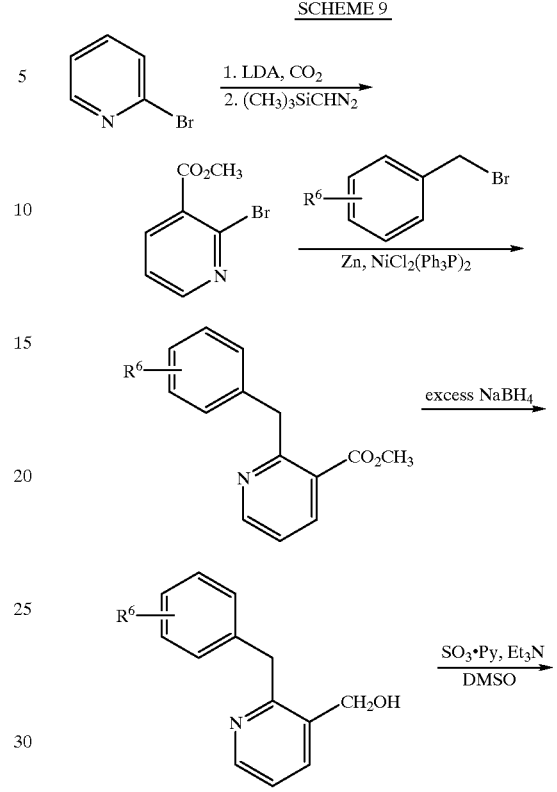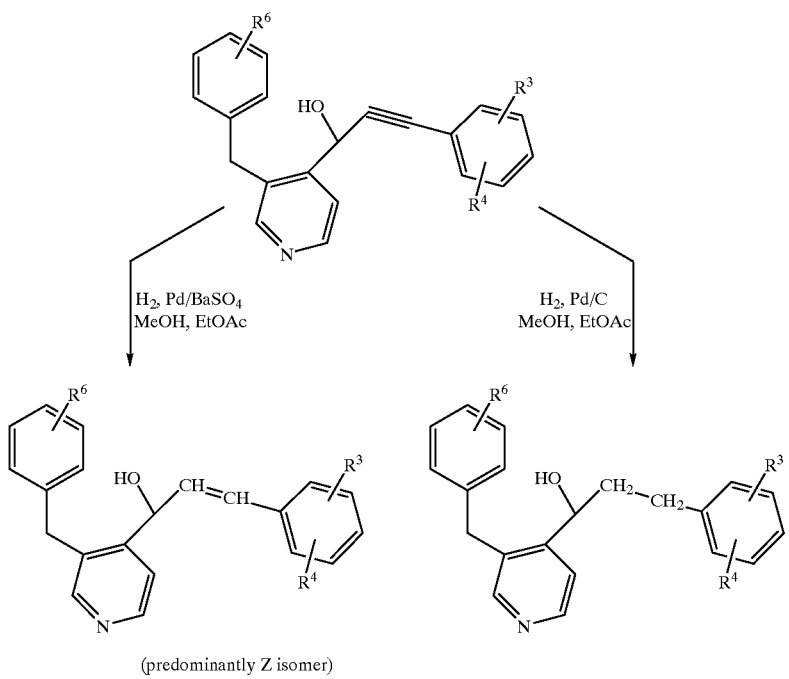

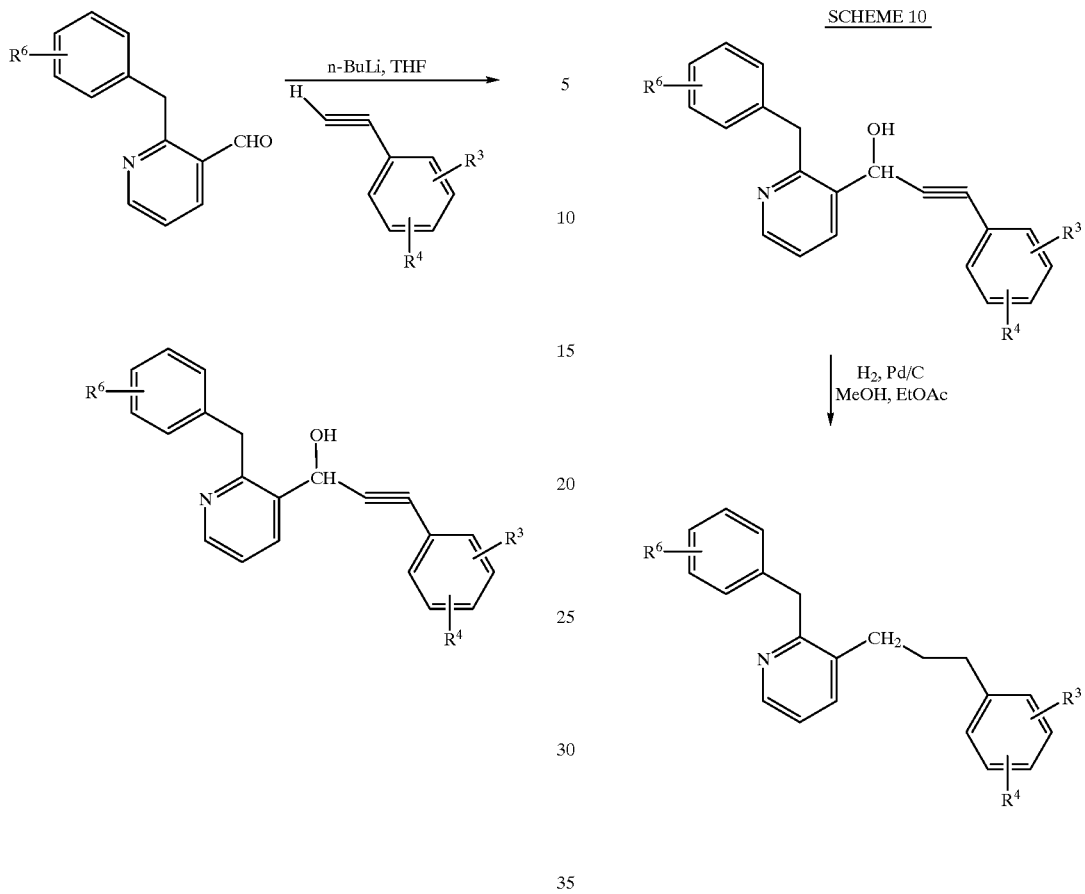
SCHEME 10
SCHEME 11

SCHEME 12
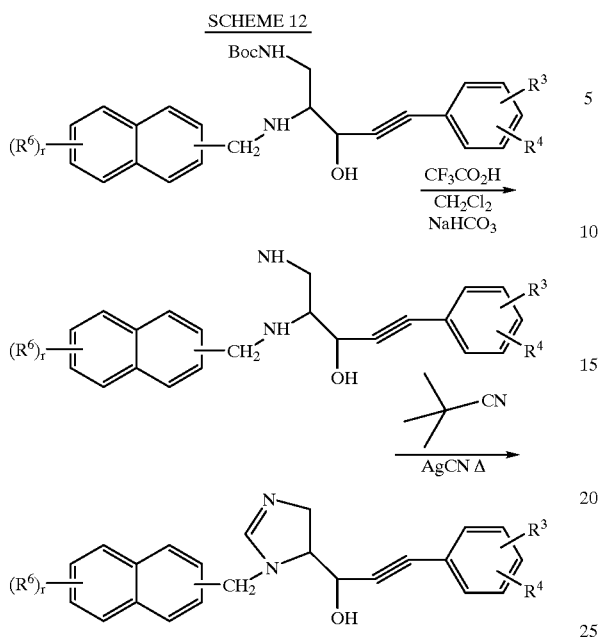
SCHEME 13
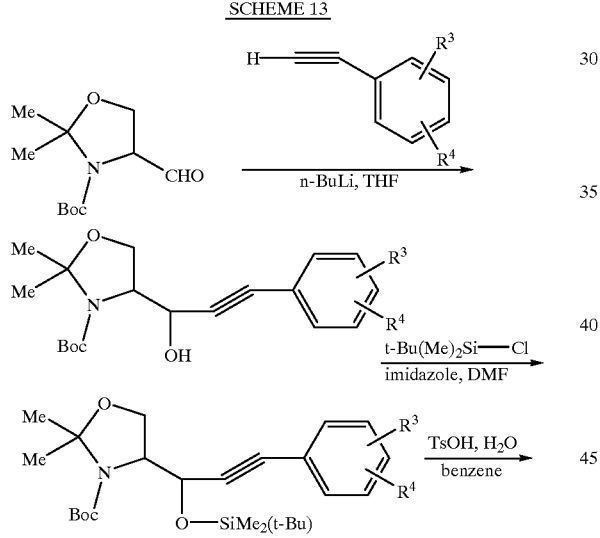
-continued
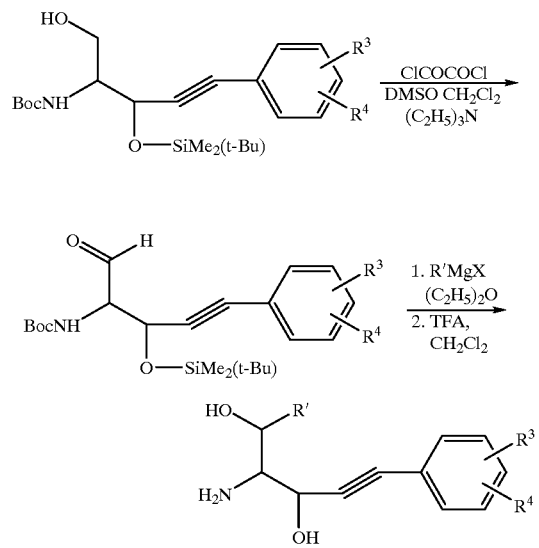
SCHEME 14
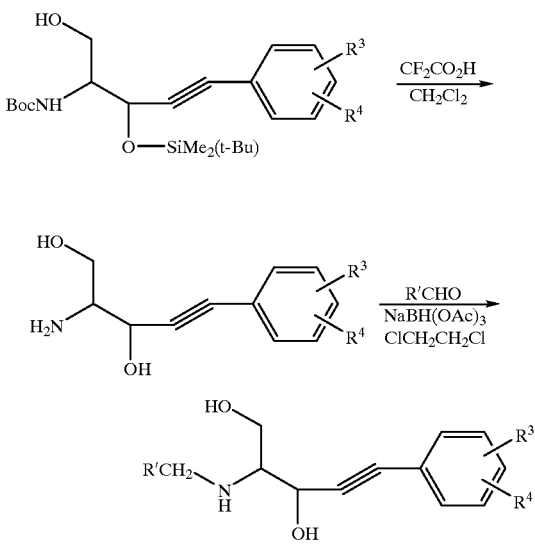
SCHEME 15
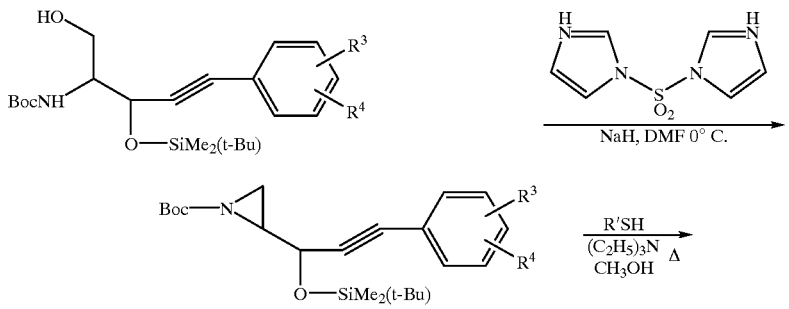

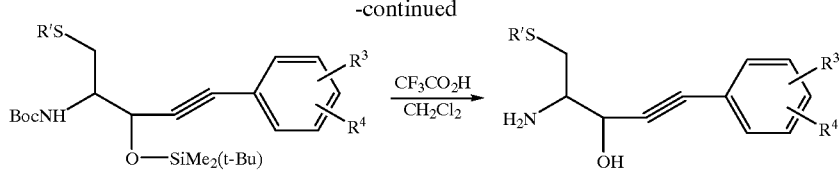

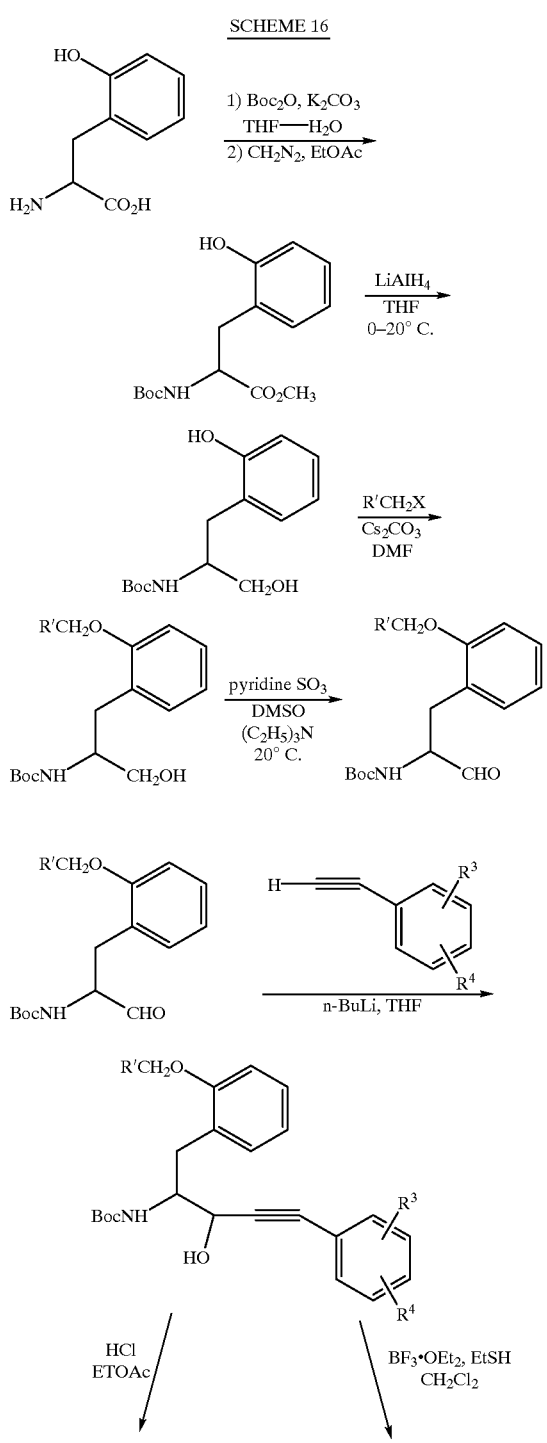

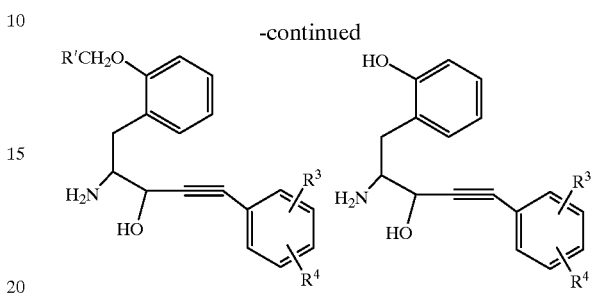

The instant compounds are useful in the treatment of cancer. Cancers which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenic properties of the instant compounds may also be useful in the treatment of certain forms of blindness related to retinal vascularization.

The compounds of this invention are also useful for inhibiting other diseases where Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, in the form of a pharmaceutical composition, which is comprised of a compound of formula I in combination with a pharmaceutically acceptable carrier. The compounds can be administered orally, topically, rectally, vaginally transdermally or parenterally, including the intravenous, intramuscular, intraperitoneal and subcutaneous routes of administration.

For oral use, the compound is administered, for example, in the form of tablets or capsules, or as a solution or suspension. In the case of tablets for oral use, carriers which are commonly used include lactose and corn starch; lubricating agents, such as magnesium stearate, are commonly added. For oral administration in capsule form, diluents also include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, the pH of the solution is suitably adjusted and the product is buffered. For intravenous use, the total concentration is controlled to render the preparation substantially isotonic.

As used herein, the term "composition" is intended to encompass a product comprising the specified ingredients in the specific amounts, as well as any product which results, directly or indirectly, from combination of the specific ingredients in the specified amounts.

The compounds of the instant invention may also be co-administered in therapeutic compositions that also contain other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ a compound of this invention substantially within the dosage range described below and other pharmaceutically active agent(s) typically within the acceptable dosage range. Compounds of the instant invention may alternatively be used sequentially with known pharmaceutically acceptable agent(s) when a combination formulation is inappropriate.

The daily dosage will normally be determined by the prescribing physician, who may vary the dosage according to the age, weight, and response of the individual patient, as well as the severity of the patient's condition.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLE 1

(±)-1-(4-CYANOBENZYL)-5-[(1-HYDROXY-3-PHENYL)-2-PROPYNYL]IMIDAZOLE HYDROCHLORIDE

Step A: Preparation of 1-triphenylmethyl-4-(hydroxymethyl)imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl) imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder (85.8 g, 86% yield for two steps) which was sufficiently pure for use in the next reaction.

Step C: Preparation of 1-(4-cyanobenzyl)-5-(acetoxymethyl)imidazole hydrobromide A solution of the product from Step B (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid (50.4 g, 67% yield, 89% purity by HPLC) which was used in the next step without further purification.

Step D: Preparation of 1-(4-cyanobenzyl)-5-(hydroxymethyl)imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. $NaHCO_3$ and brine. The solution was then dried ($Na_2SO_4$), filtered, and concentrated in vacuo to provide the crude product (26.2 g, 82% yield) as a pale yellow fluffy solid which was sufficiently pure for use in the next step without further purification.

Step E: Preparation of 1-(4-cyanobenzyl)-5-imidazolecarboxaldehyde

To a solution of the alcohol from Step D (21.5 g, 101 mmol) in 500 mL of DMSO at room temperature was added triethylamine (56 mL, 402 mmol), then $SO_3$-pyridine complex (40.5 g, 254 mmol). After 45 minutes, the reaction was poured into 2.5 L of EtOAc, washed with water (4×1 L) and brine, dried ($Na_2SO_4$), filtered, and concentrated in vacuo to provide the aldehyde (18.7 g, 88% yield) as a white powder which was sufficiently pure for use in the next step without further purification.

Step F: Preparation of (±)-1-(4-cyanobenzyl)-5-[(1-hydroxy-3-phenyl)-2-propynyl]imidazole hydrochloride To a solution of phenylacetylene (0.172 mL, 1.56 mmol) in 5 mL of THF at 0° C. was added n-butyllithium (0.530 mL, 2.5 M in hexanes, 1.32 mmol). After 15 minutes, the aldehyde from Step E (254 mg, 1.20 mmol) was added, and the reaction was stirred for 30 minutes. The reaction was quenched with sat. aq. $NaHCO_3$, poured into EtOAc, washed with sat. aq. $NaHCO_3$ and brine, dried ($Na_2SO_4$), filtered, and concentrated in vacuo. The resulting product was purified by silica gel chromatography (35–50% acetone/$CH_2Cl_2$) to provide 187 mg of the desired alcohol. A portion of this was taken up in $CH_2Cl_2$ and treated with excess 1 M HCl/ether solution, and concentrated in vacuo. The titled product hydrochloride was isolated as a white solid.

FAB mass spectrum m/e 314 (M+1). Analysis calculated for $C_{20}H_{15}N_3O$·1.0 HCl·0.90 $H_2O$: C, 65.63; H, 4.90; N, 11.48; Found: C, 65.81; H, 4.98; N, 11.17.

EXAMPLE 2

(±)-1-(4-CYANOBENZYL)-5-[(1-HYDROXY-4-PHENYL)-3-BUTYNYL]IMIDAZOLE HYDROCHLORIDE

To a solution of t-butyllithium in 1.5 mL of THF (0.78 mL of 1.7 M in pentane, 1.32 mmol) at −78° C. was added tetramethylethylenediamine (0.199 mL, 1.32 mmol) and 1-phenyl-1-propyne (0.150 mL, 1.20 mmol). The solution was warmed to 0° C. for one hour, then cooled to −78° C. The aldehyde from Step E of Example 1 (225 mg, 1.07 mmol) on 1.0 mL THF was added, and the reaction allowed to warm to 0° C. After 30 minutes, the reaction was quenched with sat. aq. $NaHCO_3$, poured into EtOAc, washed with sat. aq. $NaHCO_3$ and brine, dried ($Na_2SO_4$), filtered, and concentrated in vacuo. The product was purified by silica gel chromatography (3–4% MeOH/$CH_2Cl_2$), then taken up in $CH_2Cl_2$ and treated with excess 1 M HCl/ether solution, and concentrated in vacuo to provide the titled product hydrochloride (48 mg) as a pale yellow foam.

FAB mass spectrum m/e 328 (M+1). Analysis calculated for $C_{21}H_{17}N_3O$·1.10 HCl·0.10 $Et_2O$: C, 68.56; H, 5.14; N, 11.21; Found: C, 68.30; H, 5.04; N, 11.06.

EXAMPLE 3

(±)-3-(4-CYANOBENZYL)-4-[(1-HYDROXY-3-PHENYL)-2-PROPYNYL]PYRIDINE HYDROCHLORIDE

Step A: Preparation of 3-(4-cyanobenzyl)pyridin-4-carboxylic acid methyl ester

A solution of 4-cyanobenzyl bromide (625 mg, 3.27 mmol) in dry THF (4 mL) was added slowly over 3 min. to a suspension of activated Zn (dust; 250 mg) in dry THF (2 mL) at 0° under an argon atmosphere. The ice-bath was removed and the slurry was stirred at room temperature for a further 30 min. Then 3-bromopyridin-4-carboxylic acid methyl ester (540 mg. 2.5 mmol) followed by dichlorobis(triphenylphosphine)nickel (II) (50 mg). The resultant reddish-brown mixture was stirred for 3 h at ~40–45° C. The mixture was cooled and distributed between EtOAc (100 ml) and 5% aqueous citric acid (50 mL). The organic layer was washed with $H_2O$ (2×50 mL), dried with $Na_2SO_4$. After evaporation of the solvent the residue was purified on silica gel, eluting with 35% EtOAc in hexane to give 420 mg as a clear gum. FAB ms (M+1) 253.

Step B: Preparation of 3-(4-cyanobenzyl)-4-(hydroxymethyl)pyridine

The title compound was obtained by sodium borohydride (300 mg) reduction of the ester from Step A (415 mg) in methanol (5 mL) at room temperature. After stirring for 4 h the solution was evaporated and the product was purified on silica gel, eluting with 2% methanol in chloroform to give the title compound. FAB ms (M+1) 225.

Step C: Preparation of 3-(4-cyanobenzyl)-4-pyridinal

The title compound was obtained by activated manganese dioxide (1.0 g) oxidation of the alcohol from Step B (240 mg, 1.07 mmol) in dioxane (10 mL) at reflux for 30 min. Filtration and evaporation of the solvent provided title compound, mp 80–83° C.

Step D: Preparation of (±)-3-(4-cyanobenzyl)-4-[(1-hydroxy-3-phenyl)-2-propynyl]1pyridine hydrochloride The titled compound is prepared from the pyridinal from Step C using the proceduced in Step F of Example 1. The product is purified by silica gel chromatography, then taken up in $CH_2Cl_2$ and treated with excess 1 M HCl/ether solution, and concentrated in vcacuo to provide the titled product hydrochloride.

EXAMPLE 4

1-(4-BIPHENYLMETHYL)-5-(4-CYANOBENZYL)IMIDAZOLE HYDROCHLORIDE SALT

Step A: 1-Trityl-4-(4-Cyanobenzyl)-imidazole.

To a suspension of activated zinc dust (3.57 g, 54.98mmol) in THF (50 ml)was added dibromoethane (0.315 ml, 3.60 mmol) and the reaction stirred under argon at 20° C. The suspension was cooled to 0° C. and α bromo-p-toluinitrile (9.33 g, 47.6 mmol) in THF (100 ml) was added dropwise over a period of 10 min. The reaction was then allowed to stir at 20° C. for 6 hr and bis(triphenylphosphine)Nickel II chloride (2.4 g, 3.64 mmol)

and 5-iodotrityl imidazole (15.95 g, 36.6 mmol) was added in one portion. The resulting mixture was stirred 16 hr at 20° C. and then quenched by addition of saturated NH$_4$Cl solution (100 ml) and the mixture stirred for 2 hours. Saturated NaHCO$_3$ solution was added to give a pH of 8 and the solution was extracted with EtOAc (2×250 ml), dried MgSO$_4$ and the solvent evaporated in vacuo. The residue was chromatographed (SiO$_2$, 0–20% EtOAc/CH$_2$Cl$_2$ to afford the title compound as a white solid.

$^1$H NMR δ CDCl$_3$ (7.54 (2H, d, J=7.9 Hz), 7.38(1H, s), 7.36–7.29 (11H, m), 7.15–7.09(6H, m), 6.58(1H, s), and 3.93(2H, s))ppm.

Step B: 1-(4-Biphenylmethyl)-5-(4-cyanobenzyl)imidazole hydrochloride salt

To 1-Trityl-4-(4-Cyanobenzyl)-imidazole (608.8 mg, 1.43 mmol) in acetonitrile (2 ml) was added 4-chloromethyl biphenyl (290 mg, 1.43 mmol) and the mixture heated at 55° C. for 16 hours. The residue was dissolved in methanol (30 ml) and heated at reflux for 20 mins, cooled and evaporated to dryness. The residue was partitioned between saturated NaHCO$_3$ solution and CH$_2$Cl$_2$. The organic layer was dried (MgSO$_4$) and the solvent evaporated in vacuo. The residue was chromatographed (SiO$_2$, 5% methanol in CH$_2$Cl$_2$) to afford the imidazole which was converted to the HCl salt by treatment with one equivalent of HCl in aqueous acetonitrile. Evaporation of solvent in vacuo afforded the title compound as a white powder.

Anal. Calcd for C$_{24}$H$_{19}$N$_3$·1.00 HCl: C, 74.70; H, 5.22; N, 10.89. Found: C, 74.70; H, 5.31; N, 10.77. FAB MS 350 (MH$^+$).

$^1$H NMR CD$_3$OD δ 9.03(1H, s), 7.65–7.50(5H, m), 7.44 (2H, t, J=7.5 Hz), 7.39(1H, s), 7.35(1H, t, J=7.3 Hz), 7.26(2H, d, J=8.1 Hz), 7.20(2H, d, J=8.1 Hz), 5.42(2H, s), and 4.17(2H, s) ppm.

EXAMPLE 5

[1-(4-CYANOBENZYL)IMIDAZOL-5-YL]([1,1'-BIPHENYL]-4-YL)METHANOL

A Grignard reagent, freshly prepared from 4-bromo[1,1'-biphenyl] (116 mg, 500 μmol) and magnesium turnings (18 mg, 730 μmol) in dry THF (500 μl) was added to a dry Argon-purged 3 mL flask containing the aldehyde (105 mg, 500 μmol) in dry THF (200 μL) with vigorous stirring at room temperature. After 1 hour the reaction was quenched with sat. NH$_4$Cl (5 mL) and distributed between EtOAc (50 mL) and H$_2$O (50 mL). The organic phase was evaporated and the residue was chromatographed on silica gel (CHCl$_3$-MeOH (20:1)) to yield title (117 mg).

FAB ms (M+1) 366.25. Anal. Calc. for C$_{24}$H$_{19}$N$_3$O·0.10 CHCl$_3$·0.10 CH$_3$OH; C, 76.37; H, 5.16; N, 11.04. Found: C, 76.13; H, 5:10; N, 10.76.

EXAMPLE 6

[1-(4-CYANOBENZYL)IMIDAZOL-5-YL]([1,1'-BIPHENYL]-4-YL)KETONE

The alcohol (Example 5) (105 mg, 228 μmol) was added to dioxane (3 mL) and activated MnO$_2$ (300 mg) and the black mixture was stirred at reflux for 2 hr. The mixture was filtered and the clear filtrate was evaporated and the residue was chromatographed on silica gel (CHCl3-MeOH (30:1)) to yield title (35 mg).

FAB ms (M+1) 364.07. Anal. Calc. for C$_{24}$H$_{17}$N$_3$O·0.35 CHCl$_3$; C, 72.17; H, 4.32; N, 10.37. Found: C, 71.87; H, 4.45; N, 10.29.

EXAMPLE 7

1-{[1-(4-CYANOBENZYL)-1H-IMIDAZOL-5-YL]ETHYL}-4-PHENYL IMIDAZOLE BIS HYDROCHLORIDE SALT

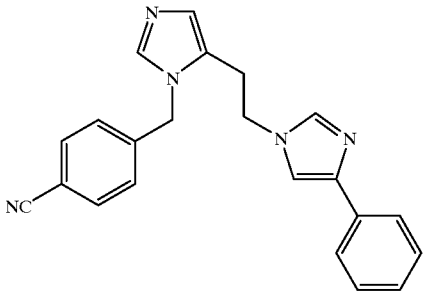

Step A: 1H-Imidazole-4-acetic acid methyl ester hydrochloride

A solution of 1H-imidazole-4-acetic acid hydrochloride (4.00 g, 24.6 mmol) in methanol (100 ml) was saturated with gaseous hydrogen chloride. The resulting solution was allowed to stand at room temperature for 18 hrs. The solvent was evaporated in vacuo to afford the title compound as a white solid.

$^1$H NMR CDCl$_3$, δ 8.85(1H, s), 7.45(1H, s), 3.89(2H, s) and 3.75(3H, s) ppm.

Step B: 1-(Triphenylmethyl)-1H-imidazol-4-ylacetic acid methyl ester

To a solution of the product from Step A (24.85 g, 0.141 mol) in DMF (115 ml) was added triethylamine (57.2 ml, 0.412 mol) and triphenylmethyl bromide (55.3 g, 0.171 mol) and the suspension was stirred for 24 hrs. After this time, the reaction mixture was diluted with EtOAc and water. The organic phase was washed with saturated aqueous NaHCO$_3$, dried (Na$_2$SO$_4$) and the solvent evaporated in vacuo. The residue was purified by chromatography (SiO$_2$, gradient elution, 0–100% EtOAc in hexanes;) to provide the title compound as a white solid.

$^1$H NMR CDCl$_3$, δ 7.35(1H, s), 7.31(9H, m), 7.22(6H, m), 6.76(1H, s), 3.69(3H, s) and 3.60(2H, s) ppm.

Step C: [1-(4-Cyanobenzyl)-1H-imidazol-5-yl]acetic acid methyl ester.

To a solution of the product from Step B (8.00 g, 20.9 mmol) in acetonitrile (70 ml) was added 4-cyanobenzyl bromide (4.10 g, 20.92 mmol) and heated at 55° C. for 3 hr. After this time, the reaction was cooled to room temperature and the resulting imidazolium salt was collected by filtration. The filtrate was heated at 55° C. for 18 hrs. The reaction mixture was cooled to room temperature and evaporated in vacuo. To the residue was added EtOAc (70 ml) and the resulting precipitate collected by filtration. The precipitated imidazolium salts were combined, suspended in methanol (100 ml) and heated to reflux for 30 min. After this time, the solvent was removed in vacuo,. The resulting residue was suspended in EtOAc (75 ml) and the solid isolated by filtration and washed with EtOAc. The solid was treated with saturated aqueous NaHCO$_3$ solution (300 ml) and CH$_2$Cl$_2$ (300 ml) and stirred at room temperature for 2 hrs. The organic layer was separated, dried (MgSO$_4$) and evaporated in vacuo to afford the title compound as a white solid $^1$HNMR CDCl$_3$, δ 7.65(1H, d, J=8 Hz), 7.53(1H, s), 7.15(1H, d, J=8 Hz), 7.04(1H, s), 5.24(2H, s), 3.62(3H, s) and 3.45(2H, s) ppm.

Step D: 5-[1-(4-cyanobenzyl)-1H-imidazolyl]ethanol.

To a stirred solution of the ester from example step C, (1.50 g, 5.88 mmol), in methanol (20 ml) at 0° C., was added sodium borohydride (1.00 g, 26.3 mmol) portionwise over 5 min. The reaction was stirred at 0° C. for 1 hr and then at room temperature for an additional 1 hr. The reaction was quenched by the addition of saturated NH$_4$Cl solution and the methanol evaporated in vacuo. The residue was partitioned between EtOAc and saturated NaHCO$_3$ solution and the organic extracts dried, (MgSO$_4$) and evaporated in vacuo. The residue was purified by chromatography (SiO$_2$, gradient elution, 4 to 10% methanol in methylene chloride) to afford the title compound as a white solid.

$^1$H NMR CDCl$_3$ δ 7.64(2H, d, J=8.2 Hz), 7.57(1 H, s), 7.11(2H, d, J=8.2 Hz), 6.97(1H, s), 5.23(2H, s), 3.79(2H, t, J=6.2 Hz), 2.66(2H, t, J=6.2 Hz) ppm.

Step E: 5-(-1-(4-Cyanobenzyl)-imidazolyl) ethylmethanesulfonate.

A solution of 5-[1-(4-cyanobenzyl)-1H-imidazolyl] ethanol (0.500 g, 2.20 mmol) in methylene chloride (6 ml) at 0° C. was treated with Hunig's base (0.460 ml, 2.64 mmol) and methanesulfonyl chloride (0.204 ml, 2.64 mmol). After 2 hrs, the reaction was quenched by addition of saturated NaHCO$_3$ solution (50 ml) and the mixture extracted with methylene chloride (50 ml), dried (MgSO$_4$) and the solvent evaporated in vacuo. The title compound was used without furthur purification.

$^1$H NMR CDCl$_3$ δ 7.69 (1H, s) 7.66(2H, d, J=8.2 Hz), 7.15 (2H, d, J=8.2 Hz), 7.04(1H, s), 5.24(2H, s), 4.31(2H, t, J=6.7 Hz), 2.96(3H, s), and 2.88(2H, t, J=6.6 Hz)ppm.

Step F: 1-{[1-(4-Cyanobenzyl)-1H-imidazol-5-yl]ethyl}-4-phenyl imidazole bis hydrochloride salt.

To a suspension of sodium hydride (14.2 mg, 60% dispersion in mineral oil, 0.356 mmol) in DMF (0.30 ml) at 0° C. was added 4-phenyl imidazole (48.8 mg, 0.339 mmol), and stirred for 20 mins. A solution of the mesylate from step E (100 mg, 0.339 mmol) in DMF (0.50 ml) was added to the solution and stirring continued at 0° C. for 1 hr and then at room temperature for 16 hrs. The reaction was quenched with saturated ammonium chloride solution (0.10 ml), and the the solvent evaporated in vacuo. The residue was purified by chromatography (SiO$_2$, gradient elution, 2–5% ammonium hydoxide: acetonitrile. The resulting material was converted to the HCl salt by treating an EtOAc solution of the imidazole with gasseous HCl and evaporating the solvent in vacuo.

Anal. Calcd for C$_{22}$H$_{19}$N$_5$·2.00HCl·1.50H$_2$O: C, 58.29; H, 5.34; N, 15.45. Found: C, 58.24; H, 5.47; N, 15.48. FAB HRMS exact mass calcd for C$_{22}$H$_{20}$N$_5$ 354.171871 (MH$^+$); found 354.171948.

$^1$H NMR CD$_3$OD δ 8.93 (1H, s), 8.75(1H, s), 7.86(1H, s), 7.76(2H, d, J=7.9 Hz), 7.69(2H, d, 7.1 Hz), 7.65–7.35(6H, m), 5.61(2H, s) and 4.53(2H,m)ppm.

In vitro inhibition of ras farnesyl transferase

Assays of farnesyl-protein transferase.

Partially purified bovine FPTase and Ras peptides (Ras-CVLS, Ras-CVIM and Ras-CAIL) were prepared as described by Schaber et al. *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in the above Examples 1–7 were tested for inhibitory activity against human FPTase by the assay described above and were found to have IC$_{50}$ of 50 μM.

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/ SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

In Vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×104 cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound represented by formula I:

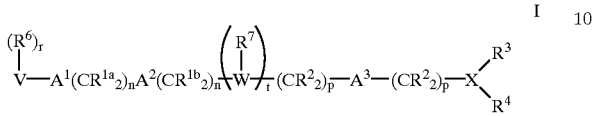

or a pharmaceutically acceptable salt thereof, wherein:

$R^{1a}$, $R^{1b}$ and $R^2$ are independently selected from the group consisting of: hydrogen, aryl, substituted aryl, heterocyclyl, $C_3$–$C_{10}$ cycloalkyl, $C_2$–$C_6$ alkenyl, $C_2$–$C_6$ alkynyl, $R^8O$—, $R^9S(O)_m$— wherein m is 0, 1 or 2, $R^8C(O)NR^8$—, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl, unsubstituted or substituted by 1–3 groups selected from the group consisting of: halo, aryl, heterocyclyl, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

$R^3$ and $R^4$ are independently selected from the group consisting of: H, F, Cl, Br, —$NR^8{}_2$, $CF_3$, $NO_2$, $R^8O$—, $R^9S(O)_m$—, $R^8C(O)NH$—, $H_2NC(NH)$—, $R^8C(O)$—, $R^8C(O)$—, $N_3$, CN, $R^9OC(O)NR^8$—, $C_1$–$C_{20}$ alkyl, substituted or unsubstituted aryl and substituted or unsubstituted heterocyclyl;

$A^3$ is selected from: —C≡C—, —$R^8C$=$CR^8$—, aryl heteroaryl, —C(O)— or a bond; provided that when $A^3$ is heteroaryl, attachment of $A^3$ to the remainder of the molecule is through ring carbons of $A^3$;

X represents aryl or heteroaryl; provided that when X is heteroaryl, attachment of X the remainder of the molecule is through ring carbons of X;

$R^6$ is independently selected from the group consisting of: hydrogen, aryl, heterocyclyl, $C_3$–$C_{10}$ cycloalkyl, $C_2$–$C_6$ alkenyl, $C_2$–$C_6$ alkynyl, $C_{1-6}$ perfluoroalkyl, F, Cl, Br, $R^8O$—, $R^9S(O)_m$—, $R^8C(O)NR^8$, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl unsubstituted or substituted by 1–3 groups selected from: aryl, heterocyclyl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

$R^7$ is independently selected from the group consisting of: hydrogen, aryl, heterocyclyl, $C_3$–$C_{10}$ cycloalkyl, $C_2$–$C_6$ alkenyl, $C_2$–$C_6$ alkynyl, $C_{1-6}$ perfluoroalkyl, F, Cl, Br, $R^9O$—, $R^9S(O)_m$—, $R^8C(O)NR^8$, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl unsubstituted or substituted by 1–3 groups selected from: aryl, heterocyclyl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

each $R^8$ is independently selected from hydrogen, $C_1$–$C_6$ alkyl, aryl and aralkyl;

each $R^9$ is independently selected from $C_1$–$C_6$ alkyl and aryl;

$A^1$ and $A^2$ are independently selected from the group consisting of: a bond, —CH=CH—, —C≡C—, —C(O)—, —C(O)NR$^8$—, —NR$^8$C(O)—, —O—, —N(R$^8$)—, —S(O)$_2$N(R$^8$)—, —N(R$^8$)S(O)$_2$—, and S(O)$_m$;

V is selected from the group consisting of: hydrogen, heterocyclyl, aryl, $C_1$–$C_{20}$ alkyl wherein from 0 to 4 carbon atoms are replaced with a heteroatom selected from O, S, and N, and $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a ring carbon of V;

W represents heterocyclyl;

each n and p independently represents 0, 1, 2, 3 or 4;

r is 0 to 5, provided that r is 0 when V is hydrogen, and t is 1.

2. A compound in accordance with claim 1 wherein $R^{1a}$, $R^{1b}$ and $R^2$ are independently selected from: hydrogen, —N(R$^8$)$_2$, $R^8C(O)NR^8$— or unsubstituted or substituted $C_1$–$C_6$ alkyl wherein the substituent on the substituted $C_1$–$C_6$ alkyl is selected from unsubstituted or substituted aryl, —N(R$^8$)$_2$, $R^8O$— and $R^8C(O)NR^8$—.

3. A compound in accordance with claim 1 wherein $R^3$ and $R^4$ are selected from: hydrogen, $C_1$–$C_6$ alkyl, Cl, Br, F, $R^8O$— and $CF_3$.

4. A compound in accordance with claim 1 wherein $A^3$ represents —C≡C—, —$CR^8$=$CR^8$—, —C(O)— or a bond.

5. A compound in accordance with claim 1 wherein $A^3$ represents —C(O)—.

6. A compound in accordance with claim 1 wherein $A^3$ represents aryl or heteroaryl.

7. A compound in accordance with claim 1 wherein $R^6$ represents CN.

8. A compound in accordance with claim 1 wherein $R^7$ represents hydrogen, unsubstituted or substituted $C_1$–$C_6$ alkyl.

9. A compound in accordance with claim 1 wherein $R^8$ represents H or $C_{1-6}$ alkyl, and $R^9$ is $C_{1-6}$ alkyl.

10. A compound in accordance with claim 1 wherein $A^1$ and $A^2$ are independently selected from: a bond, —C(O)NR$^8$—, —NR$^8$C(O)—, —O—, —N(R$^8$)—, —S(O)$_2$N(R$^8$)— and—N(R$^8$)S(O)$_2$—.

11. A compound in accordance with claim 1 wherein V is selected from hydrogen, heterocyclyl and aryl.

12. A compound in accordance with claim 11 wherein V is phenyl.

13. A compound in accordance with claim 1 wherein W is heterocyclyl selected from imidazolinyl, imidazolyl, oxazolyl, pyrazolyl, pyyrolidinyl, thiazolyl and pyridyl.

14. A compound in accordance with claim 1 wherein W is selected from imidazolyl and pyridyl.

15. A compound in accordance with claim 1 wherein X represents aryl.

16. A compound in accordance with claim 15 wherein X represents phenyl.

17. A compound in accordance with claim 1 wherein X represents heteroaryl.

18. A compound in accordance with claim 17 wherein X represents pyridyl.

19. A compound in accordance with claim 1 wherein m is 0 or 2.

20. A compound in accordance with claim 1 wherein n and p are 0, 1, 2 or 3.

21. A compound in accordance with claim 1 wherein t is 1.

22. A compound in accordance with claim 1 represented by formula Ia:

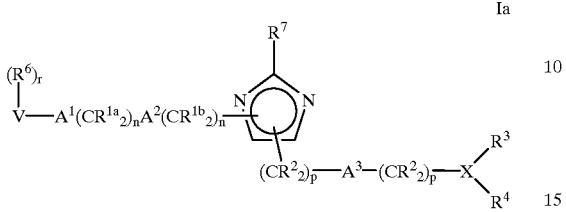

wherein:
R$^3$, R$^4$, A$^3$, R$^8$, R$^9$, X, m, n, p and r are as originally defined;
each R$^{1a}$ and R$^2$ is independently selected from hydrogen and C$_1$–C$_6$ alkyl;
each R$^{1b}$ is independently selected from: hydrogen, aryl, heterocyclyl, C$_{3-10}$ cycloalkyl, C$_{2-6}$ alkenyl, R$^8$O—, —N(R$^8$)$_2$ and C$_1$–C$_6$ alkyl unsubstituted or substituted by aryl, heterocyclyl, cycloalkyl, alkenyl, R$^8$O— and —N(R$^8$)$_2$;
R$^6$ is independently selected from: hydrogen, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, R$^8$OC(O)—, —N(R$^8$)2 and R$^9$OC(O)NR$^8$—;

R$^7$ represents H or C$_{1-6}$ alkyl;

A$^1$ and A$^2$ are independently selected from: a bond, —CH=CH—, —C≡C—, —C(O)—, —C(O)NR$^8$—, O, —N(R$^8$)— and S(O)$_m$;

and V is selected from: hydrogen; aryl; heterocyclyl selected from pyrrolidinyl, imidazolyl, pyridinyl, thiazolyl, indolyl, quinolinyl, isoquinolinyl and thienyl; C$_1$–C$_{20}$ alkyl wherein from 0 to 4 carbon atoms are replaced with a a heteroatom selected from O, S, and N, and C$_2$–C$_{20}$ alkenyl, provided that V is not hydrogen if A$^1$ is S(O)$_m$ and V is not hydrogen if A$^1$ is a bond and A$^2$ is S(O)$_m$; provided that when V is heterocycle, attachment of V to R$^8$ and to A$^1$ is through a ring carbon of V.

23. A compound in accordance with claim 1 represented by formula Ib:

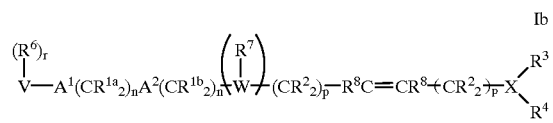

wherein:
R$^{1a}$, R$^{1b}$, R$^2$, A$^1$, A$^2$, R$^3$, R$^4$, R$^6$, R$^8$, R$^9$, X, m, n, p and r are as originally defined;
R$^7$ is selected from: hydrogen and C$_1$–C$_6$ alkyl;
V is selected from: hydrogen, heterocyclyl selected from pyrrolidinyl, imidazolyl, pyridinyl, thiazolyl, indolyl, quinolinyl, isoquinolinyl and thienyl; aryl; C$_1$–C$_{20}$ alkyl wherein from 0 to 4 carbon atoms are replaced with a heteroatom selected from O, S, and N, and C$_2$–C$_{20}$ alkenyl,
provided that V is not hydrogen if A$^1$ is S(O)$_m$ and V is not hydrogen if A$^1$ is a bond, n is 0 and A$^2$ is S(O)$_m$;
provided that when V is heterocycle, attachment of V to R$^8$ and to A$^1$ is through a ring carbon of V; and W represents heterocyclyl selected from pyrrolidinyl, imidazolyl, pyridinyl, thiazolyl, indolyl, quinolinyl and isoquinolinyl.

24. A compound in accordance with claim 1 represented by formula Ic:

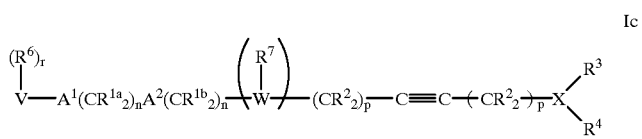

wherein:

R$^{1a}$, R$^{1b}$, R$^2$, A$^1$, A$^2$, R$^3$, R$^4$, R$^6$, R$^8$, R$^9$, X, m, n, p and r are as originally defined;

R$^7$ is selected from: hydrogen and C$_1$–C$_6$ alkyl;

V is selected from: hydrogen, heterocyclyl selected from pyrrolidinyl, imidazolyl, pyridinyl, thiazolyl, indolyl, quinolinyl, isoquinolinyl, and thienyl, aryl, C$_1$–C$_{20}$ alkyl wherein from 0 to 4 carbon atoms are replaced with a heteroatom selected from O, S, and N, and C$_2$–C$_{20}$ alkenyl,
provided that V is not hydrogen if A$^1$ is S(O)$_m$ and V is not hydrogen if A$^1$ is a bond, n is 0 and A$^2$ is S(O)$_m$;
provided that when V is heterocycle, attachment of V to R$^8$ and to A$^1$ is through a ring carbon of V; and W represents heterocyclyl selected from pyrrolidinyl, imidazolyl, pyridinyl, thiazolyl, indolyl, quinolinyl and isoquinolinyl.

25. A compound in accordance with claim 1 represented by formula Id:

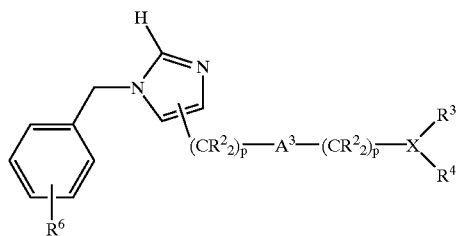

Id wherein:
each $R^2$ is independently selected from hydrogen and $C_1$–$C_6$ alkyl;

$R^3$, $R^4$, $A^3$, $R^8$, $R^9$, X, m and p are as originally defined;

and $R^6$ is selected from the group consisting of: hydrogen, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$, $R^8C(O)$—, $R^8OC(O)$—, —$N(R^8)_2$, or $R^9OC(O)NR^8$— and $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$ or $R^9OC(O)NR^8$—.

26. A compound in accordance with claim 1 represented by formula Ie:

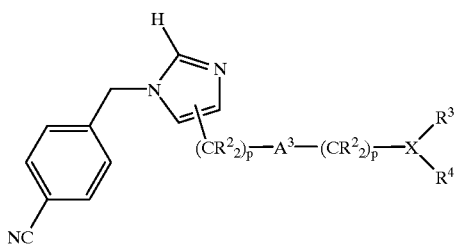

Ie wherein:
X and $A^3$ are as originally defined;

each $R^2$ is independently selected from: hydrogen and $C_1$–$C_6$ alkyl;

$R^3$ and $R^4$ are independently selected from H, F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $(R^9)OC(O)NR^8$—, $C_1$–$C_{20}$ alkyl, substituted or unsubstituted aryl, and substituted or unsubstituted heterocyclyl;

and $R^8$, $R^9$, m and p are as originally defined.

27. A compound selected from:

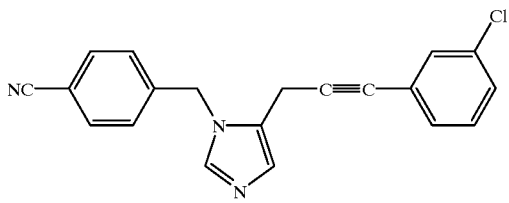

-continued

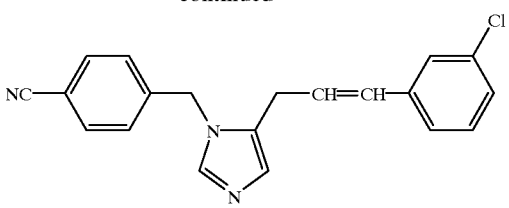

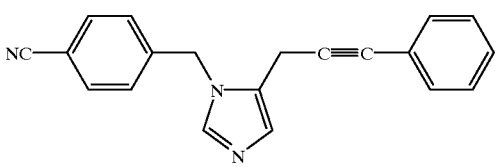

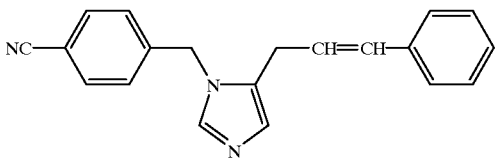

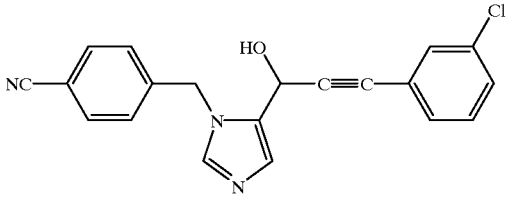

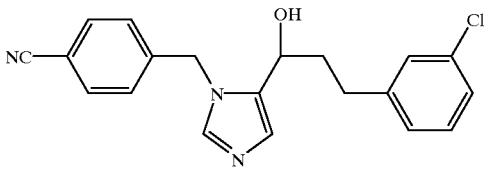

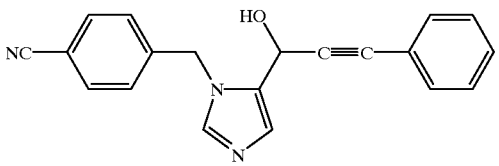

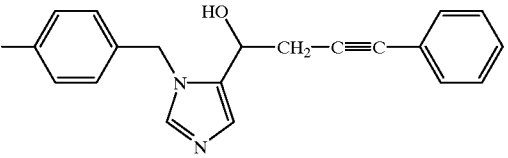

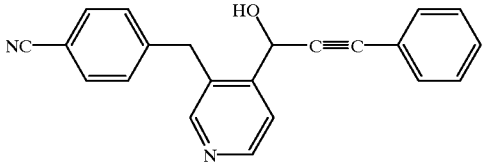

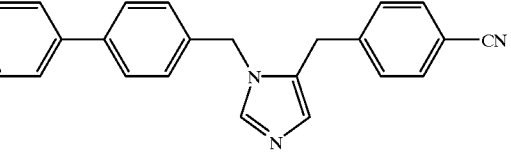

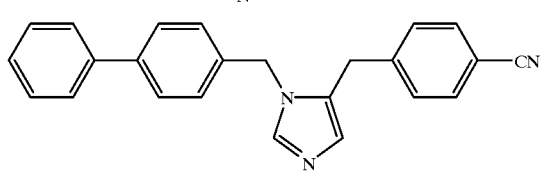

-continued

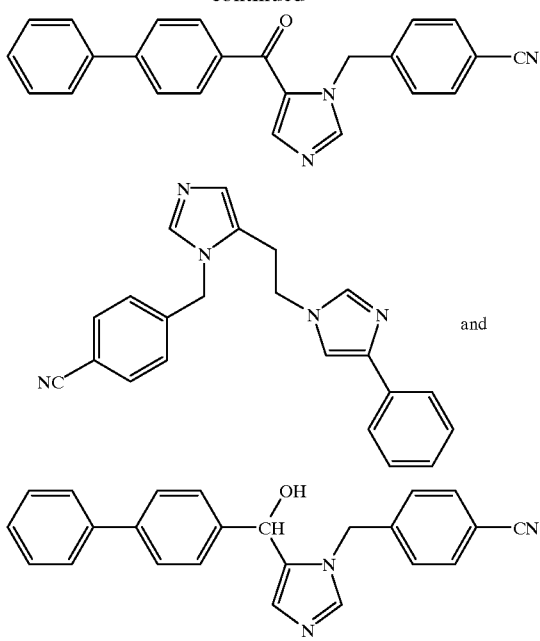

or a pharmaceutically acceptable salt thereof.

28. A pharmaceutical composition comprising a compound in accordance with claim 1 in combination with a pharmaceutically acceptable carrier.

29. A method of inhibiting farnesyl-protein transferase in a mammalian patient in need of such treatment which comprises administering to said patient an effective amount of a compound in accordance with claim 1.

30. A method of treating cancer in a mammalian patient in need of such treatment which comprises administering to said patient an anti-cancer effective amount of a compound in accordance with claim 1.

31. A method for treating neurofibromin benign proliferative disorder in a mammalian patient in need of such treatment which comprises administering to said patient an effective amount of a compound in accordance with claim 1 to treat neurofibromin benign proliferative disorder.

32. A method for treating blindness related to retinal vascularization in a mammalian patient in need of such treatment which comprises administering to said patient an effective amount of a compound in accordance with claim 1 to treat blindness related to retinal vascularization.

33. A method for treating infections from hepatitis delta and related viruses in a mammalian patient in need of such treatment which comprises administering to said patient an anti-viral effective amount of a compound in accordance with claim 1.

34. A method for preventing restenosis in a mammalian patient in need of such treatment which comprises administering to said patient a compound in accordance with claim 1 in an amount effective for preventing restenosis.

35. A method for treating polycystic kidney disease in a mammalian patient in need of such treatment which comprises administering to said patient a compound in accordance with claim 1 in an amount effective to treat polycystic kidney disease.

36. A pharmaceutical composition made by combining the compound of claim 1 and a pharmaceutically acceptable carrier.

37. A process for making a pharmaceutical composition comprising combining a compound of claim 1 and a pharmaceutically acceptable carrier.

* * * * *